United States Patent [19]
Herold

[11] Patent Number: 4,723,825
[45] Date of Patent: Feb. 9, 1988

[54] OPTICAL WAVE GUIDE FOR IRRADIATION IN DENTISTRY

[75] Inventor: Wolf-Dietrich Herold, Seefeld, Fed. Rep. of Germany

[73] Assignee: ESPE Stiftung & Co. Produktions- und Vertribs KG, Seefeld, Fed. Rep. of Germany

[21] Appl. No.: 829,077

[22] Filed: Feb. 13, 1986

[30] Foreign Application Priority Data

Feb. 15, 1985 [DE] Fed. Rep. of Germany ... 8504351[U]

[51] Int. Cl.$^4$ .............................. G02B 6/00; A61C 3/00
[52] U.S. Cl. ...................................... 350/96.1; 433/25; 433/141
[58] Field of Search ................. 350/96.1, 96.15, 96.20, 350/96.24; 433/25, 141, 229

[56] References Cited

U.S. PATENT DOCUMENTS

| | | | |
|---|---|---|---|
| 3,825,319 | 7/1974 | Cook et al. | 350/96.15 |
| 4,317,615 | 3/1982 | Herold | 350/96.1 X |
| 4,445,858 | 5/1984 | Johnson | 433/229 X |

FOREIGN PATENT DOCUMENTS

| | | |
|---|---|---|
| 0125558 | 11/1984 | European Pat. Off. |
| 7821507 | 4/1979 | Fed. Rep. of Germany |
| 2846471 | 5/1980 | Fed. Rep. of Germany ...... 433/141 |

Primary Examiner—John Lee
Assistant Examiner—John Ngo
Attorney, Agent, or Firm—Schwartz, Jeffery, Schwaab, Mack, Blumenthal & Evans

[57] ABSTRACT

An optical wave guide used for irradiation purposes in the dental field comprises a portion (10) tapering from a mean diameter at a radiation-entrance end (13) to a relatively small diameter, an intermediate portion (11) of said small diameter and curved about 90°, and a portion (12) succeeding the curved portion (11) and flaring out from said small diameter to a relatively large diameter at a radiation exit end (14) of the wave guide. Due to the fact that the curved portion (11) has a relatively small diameter it is possible also to minimize the radius of curvature of this portion without causing radiation loss. At the same time a relatively large area is obtained at the radiation-exit end (14) from which the radiation exits uniformly. The optical wave guide configured in this way is especially suitable for sealing occlusal tooth faces onto which the exit end (14) of the wave guide is flatly placed.

7 Claims, 3 Drawing Figures

OPTICAL WAVE GUIDE FOR IRRADIATION IN DENTISTRY

DESCRIPTION

The invention is directed to an optical wave guide for use with a radiation unit, particularly for dental purposes, which comprises an entrance end adapted to be coupled to a source of radiation housed in said radiation unit and an exit end adapted to be directed to a locus of irradiation, specifically a tooth face in patient's mouth. Typically, the radiation unit with the optical wave guide mounted thereon is held in the dentist's hand.

From the DE-U1 No. 7,821,507 an optical wave guide of the above type is known which is used for curing plastics fillings by means of ultraviolet radiation. For this purpose a parallel beam of rays available at the exit end of the optical wave guide and having a diameter of e.g. 8 mm will be sufficient.

The known optical wave guide is a circular cylindrical rod which in its forward portion is curved with a relatively large radius of curvature such that its exit face is inclined about an angle of approximately 50° relative to its entrance face. This shape is suitable for providing the radiation dose required for curing fillings of limited area.

Conditions are different when sealing larger tooth surfaces, especially the occlusion areas, with photopolymerizable plastic materials, where it is important for a uniform irradiation that the radiation-exit face of the optical wave guide should be held approximately parallel to the area to be irradiated. If one tries, to this end, to increase the cross-section in the known wave guide, it will become awkward to handle not only due to this measure itself but also because of the fact that with an increased light guide diameter also the radius of curvature must be increased in order to achieve in the curved portion the total internal reflection required to prevent losses of radiation. If one tried furthermore to extend the curved portion of such a wave guide over an angle of about 90°, which is appropriate for the irradiation of occlusal tooth areas, one would obtain such an inconvenient shape due to the large radius of curvature that the light guide could hardly be inserted in a patient's mouth, still less so when a child is concerned.

From the EP-A2 No. 125,558 a radiation unit for curing fillings is known in which an attempt has been made to condense a parallel beam from a lamp by means of a hollow, frusto-conical, internal mirror sleeve at the exit end thereof to a beam of low divergence and reduced cross-sectional area in order to achieve an increased curing depth by the thus obtained higher intensity. At its light-entrance end said sleeve must have a sufficiently large aperture for receiving the whole parallel beam produced by the lamp. The exit aperture of the sleeve must be sufficiently small, so that the desired condensing of the beam can be achieved. At the same time the cone angle of the sleeve must be very small so that the divergence angle of the exiting beam, which has twice the size of the cone angle of the sleeve, is maintained at the desired small value in order to prevent multiple refractions of the rays whereby the divergence angle would be multiplied. These conditions result in the sleeve becoming large and awkward to handle. Moreover, it can be proven that in practical use the curing depth cannot be increased with the known device.

It is a general object of the invention to eliminate at least some of the drawbacks which occur with comparable optical wave guides according to the prior art. In view of the above-explained prior art it is a more specific object of the invention to devise an optical wave guide in such a way that it permits irradiation of larger surfaces with optimum uniformity.

To meet with this object, the optical wave guide of the invention comprises an entrance end adapted to be coupled to a source of radiation housed in said radiation unit, an exit end adapted to be directed to a locus of irradiation, and an intermediate portion between said entrance and exit ends, the cross-section of the light guide tapering from said entrance end towards said intermediate portion and flaring out again from said intermediate portion towards said exit end.

The cross-sectional reduction of the optical wave guide from the radiation-entrance end towards the intermediate portion and the subsequent cross-sectional increase towards the radiation-exit end result in a kind of "mixing effect", wherein the individual rays of a beam of rays which is divergent at the entrance end is guided by multiple refraction within the wave guide in such a way that the radiation exits at the comparatively larger exit face with satisfactorily homogeneous intensity. The mentioned "mixing effect" is based on the fact that the radiation emanating from the radiation source and diverging at the entrance end of the wave guide is reflected with increasing steepness in the initial tapering portion of the wave guide, so that the divergence is initially increased whereas, in the subsequent flaring portion of the wave guide, the divergence of the beam of rays is partly eliminated. It has been found in practical use that, in curing certain plastics materials, the exiting beam of rays results in a highly uniform curing profile, i.e. the curing depth is the same across the entire irradiated surface. Such a uniform curing across a larger surface is important especially when tooth areas are sealed, where plastics coatings of small thickness are applied to relatively large surfaces.

In an advantageous development of the invention, the portion intermediate the tapering and flaring portions of the optical wave guide is curved. In such case, the above-mentioned "mixing effect" is further increased by the curvature so that further homogenization of the radiation intensity across the exit face may be achieved. Further, due to the fact that the curved portion is in the region of minimum cross-section of the light guide it becomes possible to minimize also the radius of curvature accordingly without having to accept any radiation losses. When used in the dental field for in-situ treatment of tooth surfaces, both the small diameter of the wave guide and the small radius of curvature of the curved portion will have the result that the front end of the wave guide, which must be inserted in the patient's mouth, is correspondingly small and handy even though the curvature extends over a considerable angle.

An embodiment in which the curved portion extends through an angle of 90° is especially appropriate because in that case, while the radiation unit may be easily handled, the radiation-exit end can readily be placed levelly on occlusal tooth areas. A diameter of about 8 to 12 mm at the entrance end of the optical wave guide is especially suitable because in that case the wave guide can readily be configured for mounting in conventional radiation units.

The optical wave guide may either be a solid rod or composed of several discrete optical fibres. The material of the solid rod or of the optical fibres may be glass, silica or synthetic plastics.

A preferred embodiment of the invention will be described in detail hereinbelow with reference to the drawing, in which.

Figure 1:
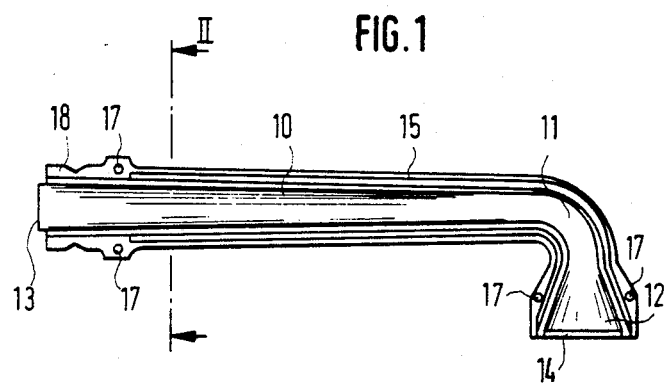
FIG. 1 is a longitudinal sectional view through an optical wave guide.

As shown in FIG. 1, an optical wave guide, which is made of a single piece of glass, silica or synthetic plastics rod, includes a tapering portion 10 which at its forward end merges into a curved portion 11 which in turn at its forward end merges into a flared portion 12. The optical wave guide has the following dimensions:

Diameter of the portion 10 at the radiation-entrance end 13: approximately 8 mm.

Diameter of the curved portion: approx. 5 mm.

Diameter of the portion 12 at the radiation-exit end 14: approximately 14 mm.

Length of the portion 10: approx. 85 mm.

Arc angle of the curved portion 11: approx. 90°.

Radius of curvature of the centre line of the optical "axis" of the curved portion: approx. 8.5 mm.

Length of the portion 12: approx. 10 mm.

The wave guide is surrounded by a protective sleeve composed of two half-shells 15, 16. The parting plane of the half-shells lies in the drawing plane of FIG. 1, in which only the rearward half-shell 15 is shown. The half-shells 15, 16 are configured and dimensioned with respect to their interior walls in such a way that they surround the wave guide with an air gap therebetween and engage the wave guide only at some few locations so as not to affect the total internal reflection.

Figure 2:
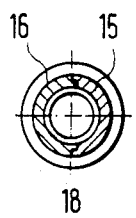
FIG. 2 is a cross-sectional view along the line II-II of FIG. 1.

As will be apparent from FIG. 2, the two half-shells 15, 16 of the protective sleeve overlap each other in the parting plane with stepped edges, which will not only prevent any escape of radiation along the seam but will also result in mutual locking of the two half-shells in the axial direction due to the curvature. For additionally joining the two half-shells, interengaging holes and locating pins such as indicated at 17 are respectively provided in the rearward and forward portions.

In the proximity of the entrance end 13 the two half-shells 15, 16 together form an annular flange 18 having an annular groove for mounting in the front end of a radiation unit (not illustrated).

Figure 3:
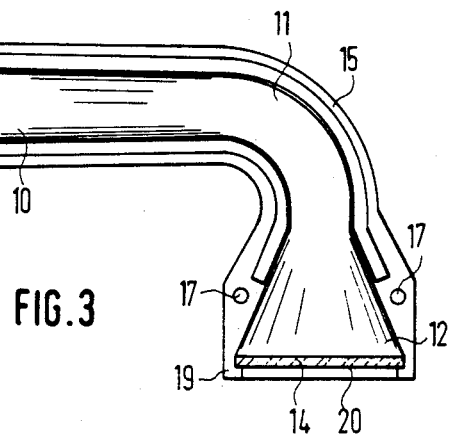
FIG. 3 is an enlarged view of the forward portion of the optical wave guide.

In the portion of the light-exit end, which is shown at a larger scale in FIG. 3, the two half-shells 15, 16 together form an inwardly directed annular flange 19 by means of which a filter plate 20 is retained at the exit end 14 of the light guide. The annular flange 19, which extends beyond the exit end in axial direction, simultaneously excludes any escape of radiation transversely to the optical axis which could affect the operator during work.

In the above description the invention has been explained with particular reference to an optical wave guide for use in dental practice. However, the invention is not limited to this field. Optical wave guides in accordance with the invention may also be used in other technical fields, for instance for curing adhesives, such as in the electrotechnical field and in civil engineering.

I claim:

1. An optical wave guide used for irradiation purposes, particularly in the dental field, comprising:
   (a) an entrance end connectable to a source of radiation, said entrance end having a diameter of about 8 to about 12 mm,
   (b) an exit end which can be positioned at the locus of irradition, said exit end being larger in diameter than the diameter of said entrance end, and
   (c) an intermediate curved portion between said entrance and exit ends, the cross-section diameter of the wave guide tapering from said entrance end towards said intermediate portion, being the most reduced in such intermediate portion, and then flaring out toward said exit end at which the diameter of said guide is the greatest.

2. An optical wave guide as claimed in claim 1, wherein said intermediate curved portion has a diameter of about 4 to about 6 mm, perferably about 5 mm.

3. An optical wave guide as claimed in claim 1, wherein said intermediate curved portion extends through an angle of about 90°.

4. An optical wave guide as claimed in claim 1, wherein the radius of curvature of said intermediate curved portion, as measured from its center line, is about 7 to about 10 mm, preferably about 8.5 mm.

5. An optical wave guide as claimed in claim 1, wherein said exit end has a diameter of about 10 to about 20 mm, preferably about 14 mm.

6. An optical wave guide as claimed in claim 1, further including a filter mounted at said exit end, said filter being supported in a protective sleeve surrounding said wave guide.

7. An optical wave guide as claimed in claim 1 wherein said guide comprises a solid rod.

* * * * *